United States Patent [19]
D'Amelio et al.

[11] Patent Number: 5,647,840
[45] Date of Patent: Jul. 15, 1997

[54] ENDOSCOPE HAVING A DISTALLY HEATED DISTAL LENS

[75] Inventors: Frank D. D'Amelio, Solvang, Calif.; Carl J. Rebert, Weston; Kenneth C. Hancock, Essex, both of Conn.

[73] Assignee: Circon Corporation, Santa Barbara, Calif.

[21] Appl. No.: 306,268

[22] Filed: Sep. 14, 1994

[51] Int. Cl.⁶ ............................................. A61B 1/07
[52] U.S. Cl. ........................ 600/169; 600/182; 600/176
[58] Field of Search .......................... 600/169, 175, 600/176, 182; 392/408, 409; 359/512

[56] References Cited

U.S. PATENT DOCUMENTS

| | | | |
|---|---|---|---|
| 4,279,246 | 7/1981 | Chikama | 600/169 |
| 5,009,655 | 4/1991 | Daignault, Jr. et al. | 606/7 |
| 5,207,213 | 5/1993 | Auhll et al. | 600/157 |

*Primary Examiner*—Richard J. Apley
*Assistant Examiner*—John Leubecker
*Attorney, Agent, or Firm*—Daniel J. Meaney, Jr.

[57] ABSTRACT

An endoscope having a distally heated distal lens for performing laparoscopic surgery is shown. The preferred embodiment of the endoscope is a laparoscope which includes a rigid elongated sheath tube which encloses means defining a fiber optic light carrying bundle formed of a plurality of optical fibers each of which have a distal end. The fiber optic bundle has a proximal end which is adapted to be operatively coupled to a light source having light energy including infrared radiation and a distal end which is located in the distal section of the sheath tube contiguous the distal lens. The fiber optic bundle has a selected number of the distal ends of the plurality of optical fibers treated to form an energy diverting member for directing thermal or infrared energy from a light source into the periphery of the distal lens to increase the temperature thereof to resist fogging of the distal lens when the distal section of the endoscope is inserted into a warm, moist area such as a body cavity. The laparoscope may include a fluid flow channel which terminates in a nozzle located at the distal tip for directing a fluid flow across the distal lens to remove image impeding material therefrom. The fluid is usually at a cooler temperature and the application of the cooler fluid to the distal ends necessitates the need for continuous heating of the distal end.

49 Claims, 6 Drawing Sheets

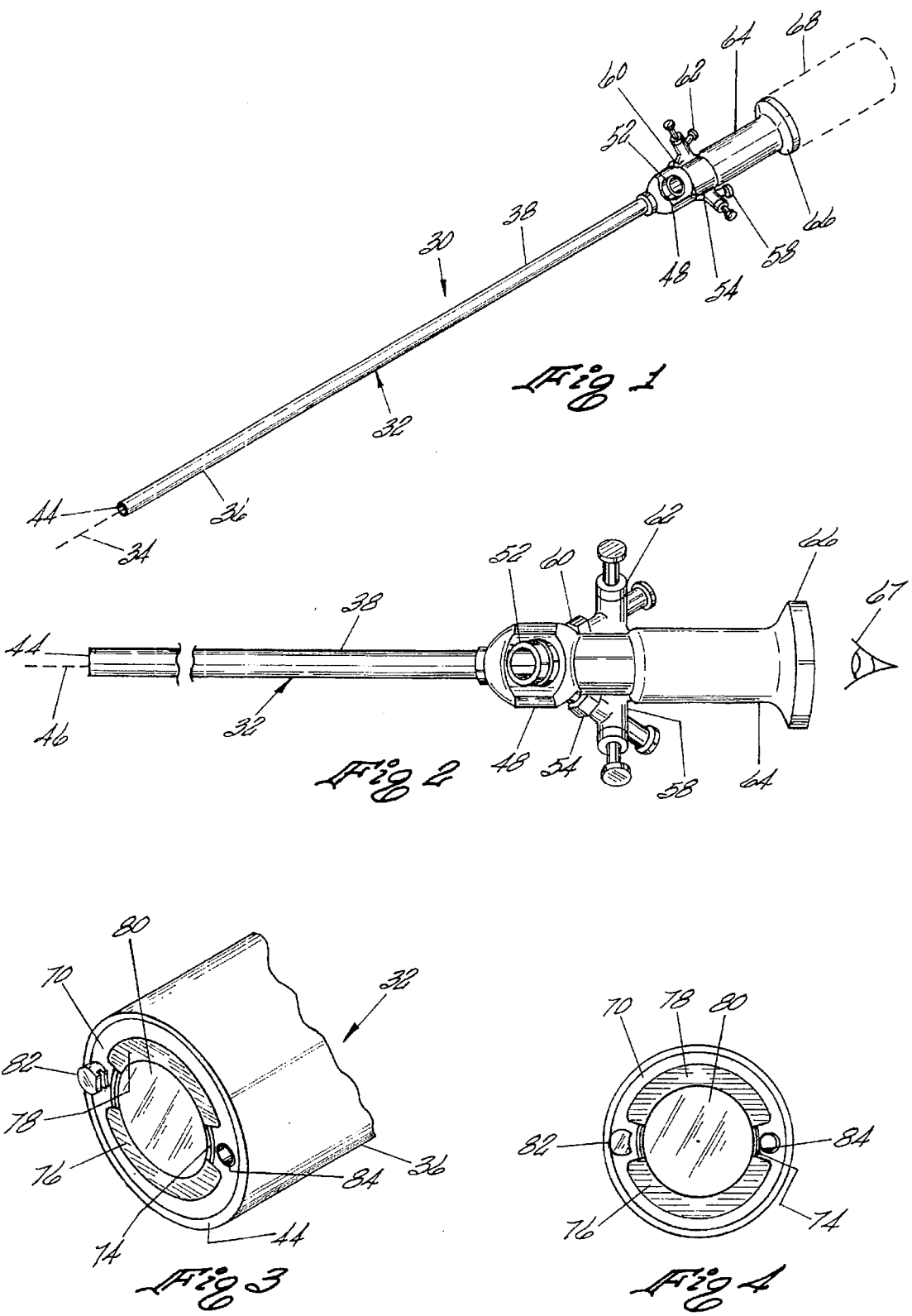

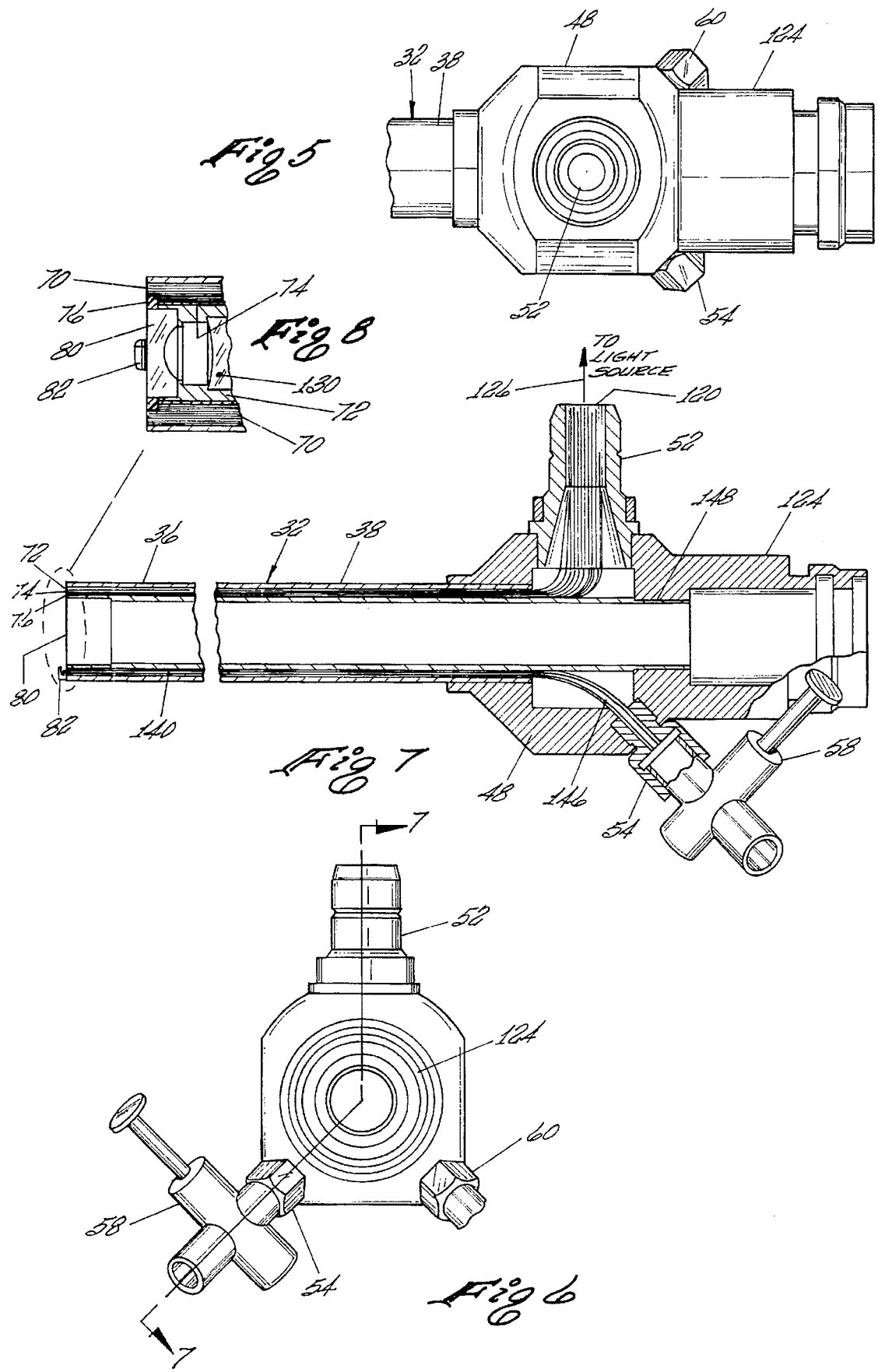

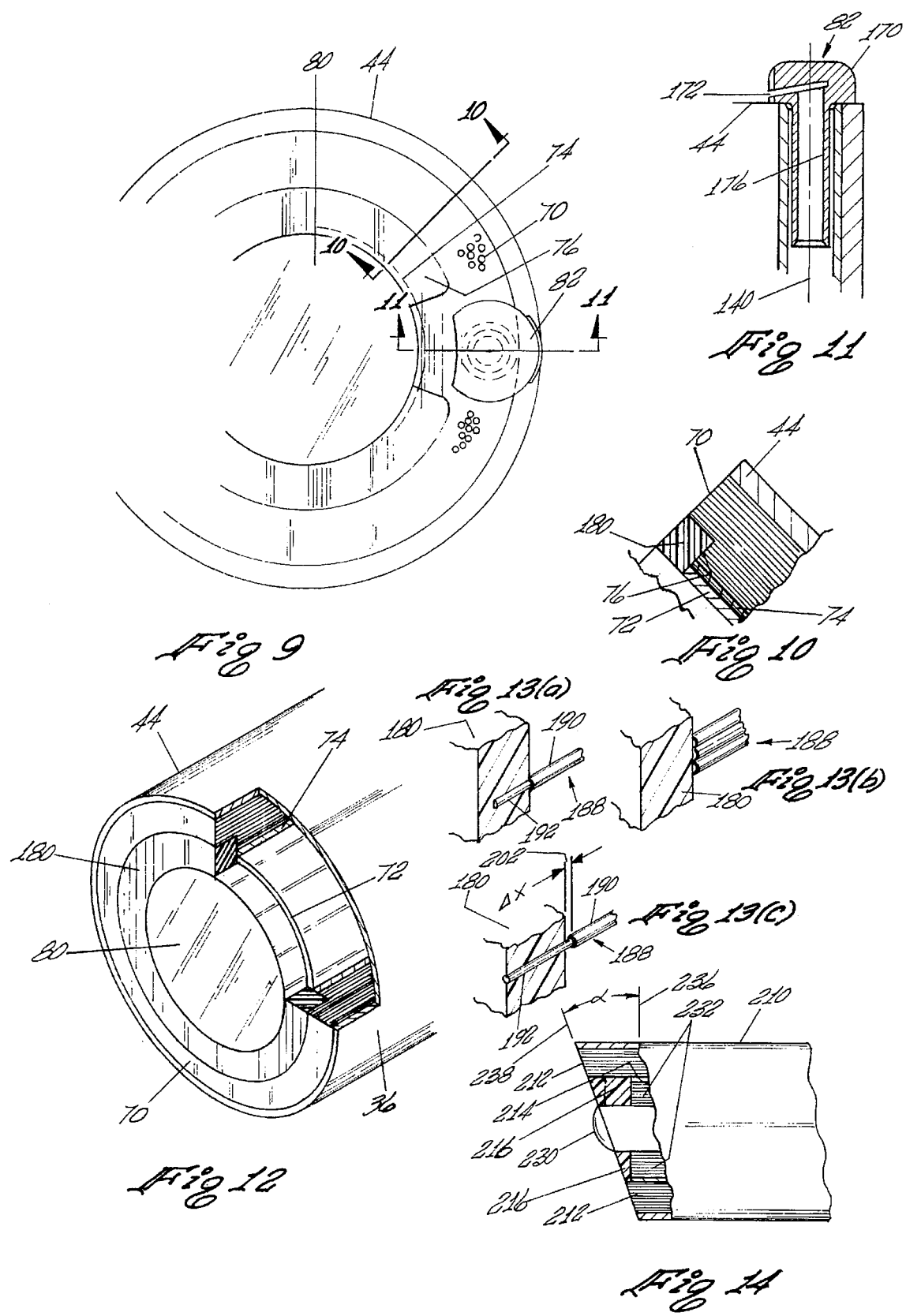

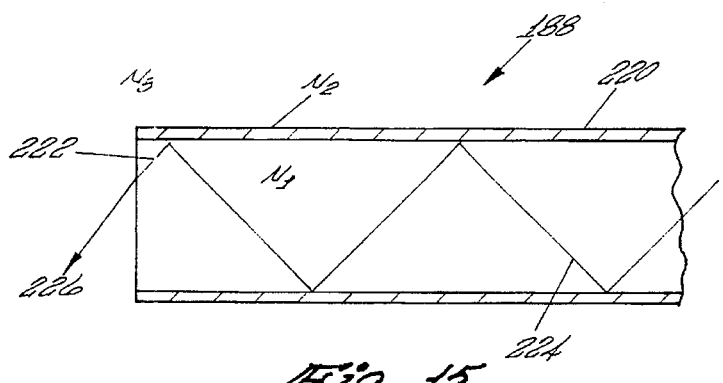
Fig 15
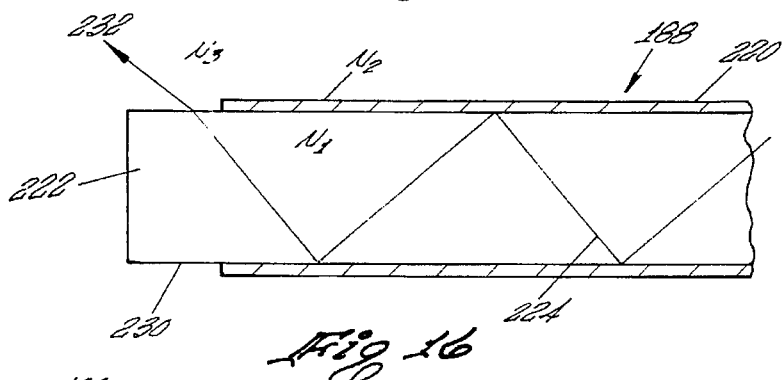
Fig 16
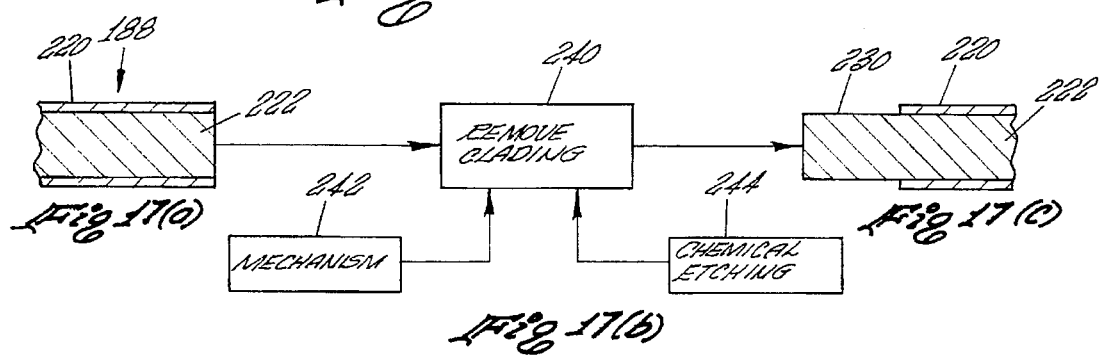
Fig 17(a)   Fig 17(b)   Fig 17(c)
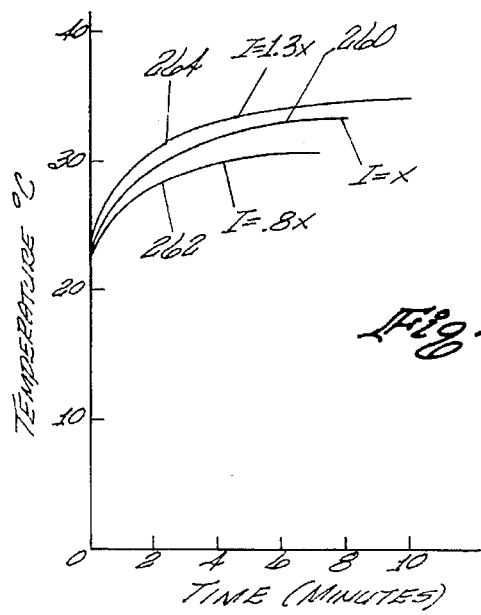
Fig 18
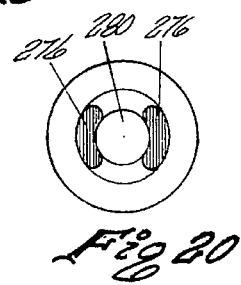
Fig 20
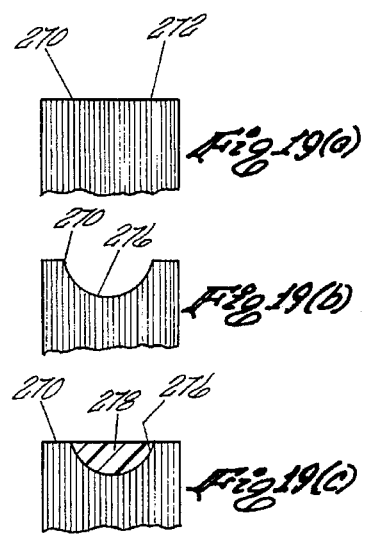
Fig 19(a)
Fig 19(b)
Fig 19(c)

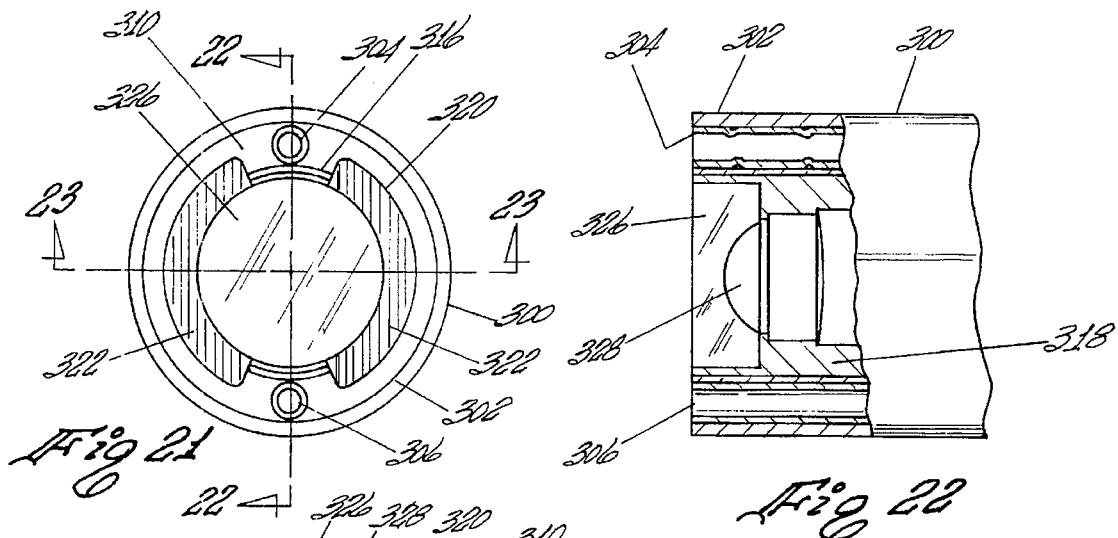
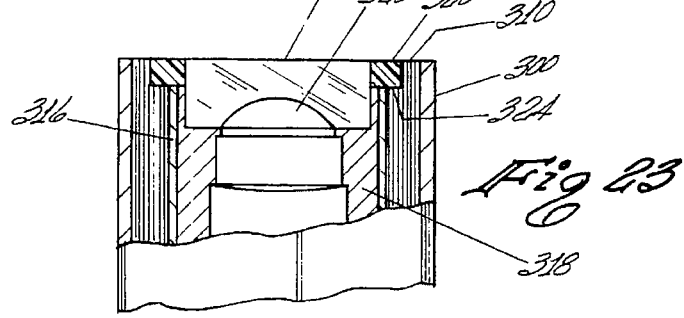
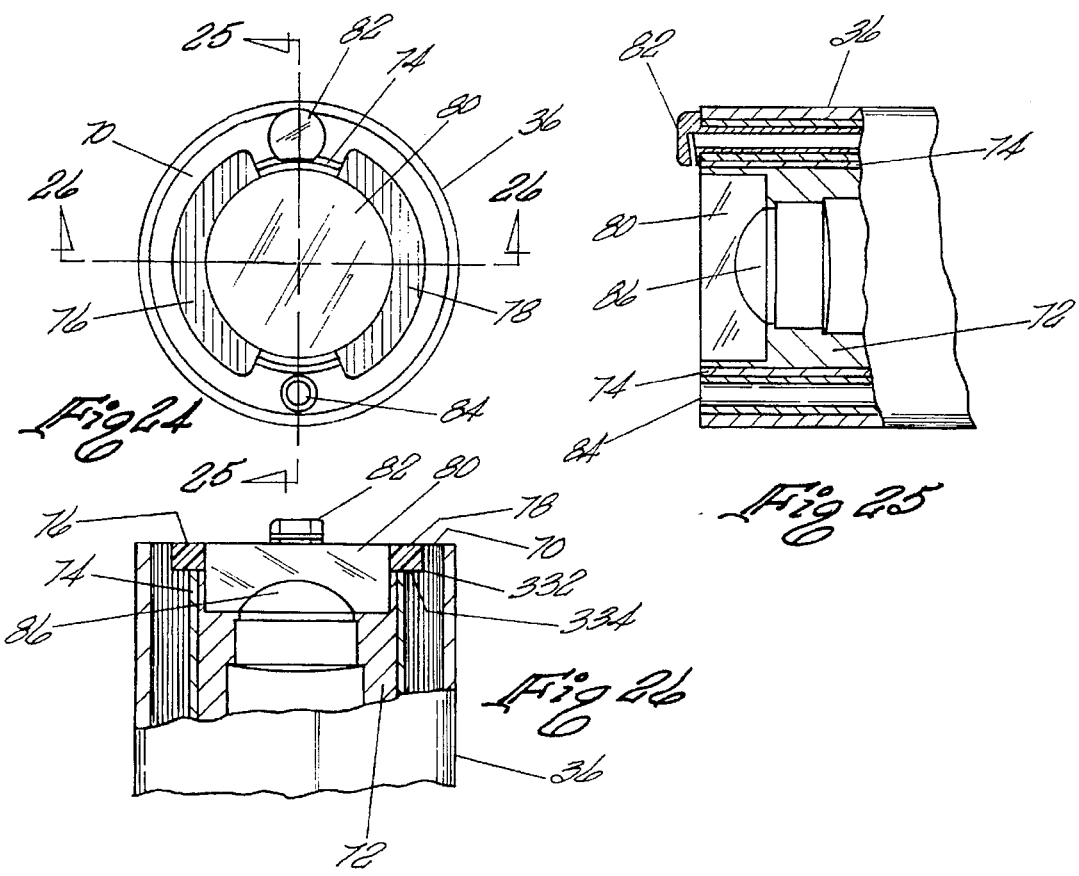

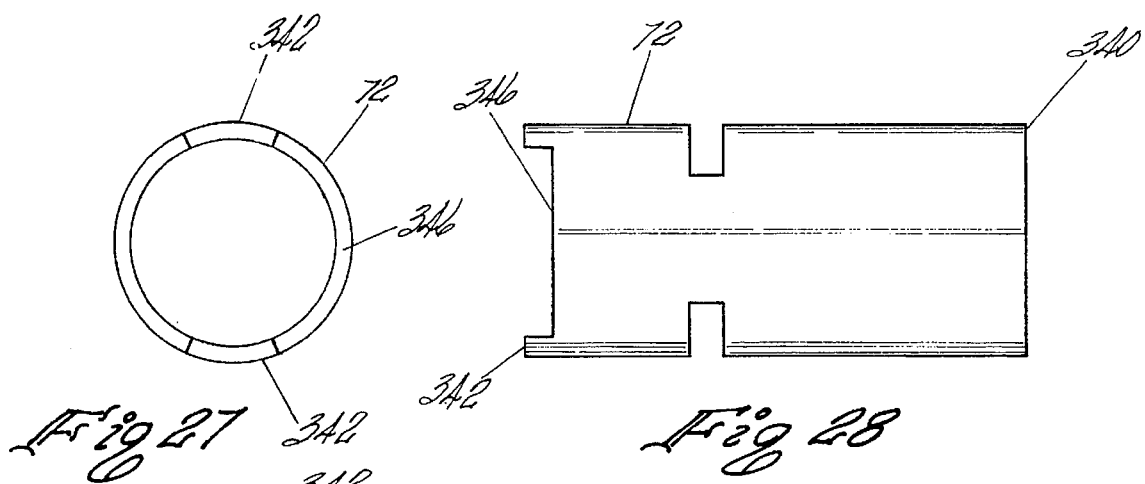
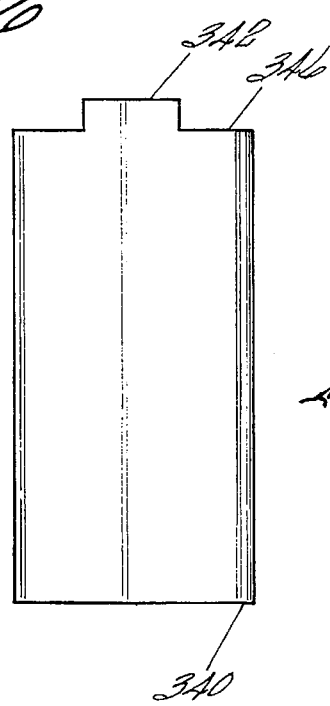
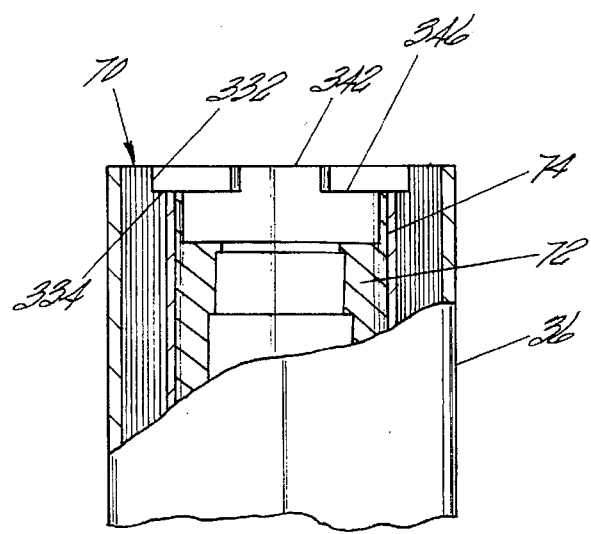

ENDOSCOPE HAVING A DISTALLY HEATED DISTAL LENS

BACKGROUND OF THE INVENTION

1. Field of the Invention

This invention relates to an endoscope or instrument which is utilized for performing procedures in a cavity and more particularly is directed to an endoscope, which in the preferred embodiment is a laparoscope having a distal tip which includes a distal optical lens and a means for utilizing a selected portion of a fiber optic light carrying bundle which passes light energy having infrared radiation. The laparoscope has a selected number of the optical fibers treated in a manner to use the same as a distal lens heating means to resist fogging of the distal lens when the distal tip of the endoscope is inserted into a warm, moist cavity, such as, for example, a body cavity. In addition, the laparoscope can include means including a fluid channel for defining a nozzle at the distal tip which is capable of directing a fluid flow across the distal lens to keep the exterior surface free from image impeding material. Additional channels, including an accessory channel, can be provided in the laparoscope to provide a stream of irrigation fluid, for applying suction to a working site or for the passage of working accessories such as laser fibers, electrosurgical probes, bi-polar probes and the like.

2. Description of the Prior Art

An endoscope is an instrument for examining the interior of a hollow cavity. Typically, an endoscope includes an optical system having a transparent member located at the distal end for passing an image. The transparent member may be a distal lens. Endoscopes are used in medical surgery and for other applications, such as, for example, inspecting the interior of a jet engine. In the medical field, one class of endoscopes are known as laparoscopes. The preferred embodiment of this invention is utilized in a laparoscope. The use of laparoscopes for performing laparoscopic procedures is well known in the art. A laparoscope is one class of an endoscope. Endoscopes are used for performing medical surgical procedures. Typically, the state-of-the-art laparoscope includes a rigid elongated sheath tube which encloses a image transferring means channel which receives a fiber optic image light bundle or relay lens system. A distal lens is typically used at the distal tip of the laparoscope to pass an image to the image transferring means. The image transferring means channel is typically surrounded by fiber optic light carrying means. The distal end of the laparoscope is used to develop an optical image of an operating site within a cavity and the operating site is illuminated by light from the fiber optic light carrying means. The optical image is transmitted through the distal lens and the image transferring means to the proximal end of the laparoscope where a viewable image is observed by the surgeon. The state-of-the-art laparoscopes are usually inserted through a cannula and trocar assembly which makes an incision or opening in the navel or belly-button of a patient. The purpose of making the incision in the navel or belly-button is to minimize the size of the surgical scar which remains upon completion of the surgical procedure. It is also known in the art to utilize a primary cannula and trocar assembly to form the initial opening through the navel or belly-button into the abdomen or the peritoneal cavity and use smaller cannula and trocar assemblies which are inserted into other smaller incisions to provide access to the peritoneal cavity for passing working tools. In the known laparoscopic procedures, the peritoneal cavity is insufflated with an appropriate fluid such as carbon dioxide ($CO_2$) gas, concomitant with laparoscopic or peritoneoscopic examination, diagnosis and/or treatment, including the excision of structures and tissues in the peritoneal cavity. In the recent past, the type of surgeries performed using laparoscopic procedures has been expanded into new minimum invasive surgical procedures. One such new procedure utilizes the laparoscope, with other appropriate instruments, for performing laparoscopic cholecystectomy which is essentially a minimum invasive surgical method for removal of a gallbladder. Similar minimum invasive surgical techniques are being developed using laparoscopes to remove other organs, such as the appendix, kidney or tissues, such as from the liver, also located in the peritoneal cavity. Also, laparoscopes are used in thoracoscopy and gynecology.

In the laparoscopic cholecystectomy procedure, the laparoscope is utilized to provide the surgeon with a video image of the operating site. The video image is provided on a color television monitor and that image is used by the surgeon to perform the procedure. To obtain the optical image, a small high sensitivity video camera is usually operatively attached to the eyepiece of the laparoscope. The surgeon is able to insert and manipulate other instruments through auxiliary cannula and trocar assemblies located at small punctures made in the abdomen, all under the view of the surgeon through the video image developed by the video camera.

As part of the laparoscopic cholecystectomy, instruments are utilized through the various small openings to place a traction on the diseased organ. Under observation of the laparoscope, the surgeon attaches clips to the arteries and ducts leading to the gallbladder and then performs an incision between the clips. By using such techniques, the gallbladder is ultimately dis-attached from the liver. Once the gallbladder has been separated from the liver, the gallbladder can then be pulled through one of the small tiny holes. The patient usually goes home the next day with usually three or four punctures which will form small scars.

The laparoscopic cholecystectomy using a laparoscope is one of the minimum invasive surgical techniques that is expected to be expanded in the future to include other surgical procedures to be performed in the peritoneal cavity, chest cavity and other cavities within the body.

It is known that when the distal tip of the laparoscope is inserted into the peritoneal cavity, a fogging or condensation occurs across the distal tip which impedes the passage of the optical image and which interferes with the ability of the surgeon to view the operating site. This fogging condition or condensation buildup is due to the fact that the operating room temperature is in the order of 20° C. (68° F.). However, the interior of the peritoneal cavity or abdomen is generally at blood temperature which is typically in the order of 37° C. (98.6° F.). Thus, when a laparoscope, which is maintained at room temperature in the operating room which is typically 20° C. has the distal tip thereof at room temperature of about 20° C. inserted into the abdomen having a temperature of approximately 37° C., the temperature differential therebetween is sufficient to cause instant fogging of the distal lens.

One known method for solving this problem art, is to heat the distal tip of the laparoscope by a variety of means. One heating method that is utilized to heat the distal tip is to insert the distal tip into a container of hot water to raise the temperature of the distal tip to approximately 37° C. Another known technique is to place the distal tip in hot towels for a sufficient period of time to raise the temperature thereof to approximately 37° C. It is desirable to keep the temperature below 42° C .because tissue damage can occur at around 42° C. Therefore, the preferred temperature is about 37° C. to avoid the possibility of the distal end damaging tissue.

Another known method for solving this problem is to use a prewarmer cap which absorbs and reflects thermal energy passed by a fiber optic light guide bundle (sometimes known as a fiber optic light carrying bundle) through an endoscope distal end to raise the temperature thereof to a level which resists fogging of the distal lens when the distal end of the laparoscope is inserted into a body cavity. The prewarmer cap is removed just before the surgical procedure begins.

Such device referred to as a Laproheater Cap is offered for sale and sold by CIRCON ACMI, located in Stamford, Conn., as Catalog No. LAPHCP.

In addition to the above fogging problem, other image impeding problems are encountered during a procedure. When a surgeon is performing a procedure, that procedure normally results in particulate matter such as protein, blood, tissue and the like, being splattered throughout the operating site during the procedure. Typically, certain of the particulate matter will adhere to the distal surface and transparent member or distal lens located at the distal tip of the laparoscope thereby impeding the transmission or passage of the optical image through the transparent member or distal lens. This is particularly true during use of laser and electrocautery procedures for removing tissue.

In a typical laparoscopic procedure, particulate matter accumulates on the distal end three or four times during a procedure. Each time the optical image is impeded by the accumulation of particulate matter, it is necessary for the surgeon to remove the laparoscope through the cannula and trocar assembly, to physically wipe the particulate matter off of the transparent member, located at the distal tip of the laparoscope, and then reinsert the laparoscope through the cannula and trocar assembly back into the abdominal or peritoneal cavity to continue the procedure.

It is also known in the art that when utilizing a laparoscope in a laparoscopic procedure, such as, for example, the laparoscopic cholecystectomy briefly described above, it is necessary that the distal lens be free from light impeding agents such as a layer of fog, protein material or organic material. It is the desire of the surgeon to keep the laparoscope in the peritoneal cavity at all times.

It is known in the field of endoscopy to utilize endoscopic instruments for performing endoscopic procedures in the upper gastrointestinal tract ("GI Tract"). In performing the endoscopic procedures in the upper GI Tract, the endoscopic procedures are generally performed using flexible instruments such as, for example, a TX-8 panendoscope (Esophago-gastro-duodenoscope) which is one of a family of panendoscopes and other gastro-intestinal endoscopes manufactured by ACMI, a predecessor to the Assignee of the present application.

The TX-8 panendoscope was designed to be used in endoscopy of the upper GI Tract. The TX-8 panendoscope was used primarily as a visualizing instrument and employing flexible optical fibers, both to transmit illumination to the operating site or area immediately in front of the endoscope and to transmit an optical image of that operating site or area from the distal tip to an eyepiece located at the proximal end of the TX-8 panendoscope. The optical image so generated by the TX-8 panendoscope was viewed by an operator or transmitted to a film or television media by means of a television camera.

In the TX-8 flexible panendoscope, vision or image impeding agents were removed from the front lens and the illumination ports by the use of air, water and suction. The air, water and suction functions were operated by finger controls located conveniently on the control head of the TX-8 panendoscope. The air input also acted as insufflation medium to improve visualization. The suction channel doubled as an end-to-end conduit through which a variety of diagnostic and therapeutic devices, such as forceps, cytology brushes, graspers and the like could be introduced into the field of view to be explored under vision control.

Another known device offered for sale and sold by the predecessor to the assignee of the present invention is a TX-6 Cannulator Duodenoscope which was utilized for endoscopic retrograde cholangio pancreatography. The TX-6 cannulator duodenoscope also included a means for removing image or vision impeding agents from the front lens and irrigation ports of the instrument.

U.S. Pat. No. 5,207,213 discloses a laparoscope having means for removing image impeding material from a distal lens.

It is also known in the art to utilize a suction-irrigation handle for endoscopic surgery of the paranasal sinuses and the anterior base of the skull. The suction irrigation handle for the endoscope is essentially a rigid sheath which receives a working telescope. The rigid sheath includes a single channel which was capable of being used for either irrigation or suction of the operative site in the paranasal sinuses or in the anterior base of the skull. The suction-irrigation handle was utilized by the surgeon to irrigate an operating site with an irrigation solution and then to remove the irrigation solution from the site.

Operating laparoscopes are also known in the art. Typically, the known operating laparoscope has a rigid elongated sheath with a rigid optical path having two prisms, a fiber optic light guide and an operating channel. The operating channel port located at the proximal end of the operating laparoscope is coaxial with the operating channel. The rigid optical path extends perpendicular (at about 90°) from the rigid elongated sheath at the proximal end and then through a 90° bend which then extends the rigid optical path along an axis which is parallel to the axis of the rigid elongated shaft terminating in an eyepiece. Prisms are used at each 90° bend of the optical path. The fiber optic light guide enters the rigid elongated sheath at the proximal end and extends from the proximal end to the distal end. The operating channel was used to pass a monopolar grasping device which was used to perform tubal ligation. Laparoscopes have been known in the art for more than ten years. The fogging of distal tip of laparoscopes has been known for a similar period of time. None of the known prior art discloses, teaches or suggests a solution to the defogging problem utilizing the fiber optic light carrying bundle as a means for raising the temperature of the distal lens in response to light energy having infrared radiation, from a light source, to a temperature level to resist fogging of the lens at the commencement of and/or during a surgical procedure including during the use of a lens washing feature when cooler irrigation fluid is applied to the distal lens for a short time duration.

SUMMARY OF THE PRESENT INVENTION

A novel, new and unique endoscope or instrument for performing laparoscopic procedures is disclosed and taught by the present invention. In the preferred embodiment, the endoscope is a laparoscope which includes a rigid elongated sheath having a selected length and a distal section. The distal section includes means for defining a distal tip which includes a fluid tight distal lens capable of passing an optical image to an image transferring means. The distal lens has an exterior surface located at the distal tip. The laparoscope further includes means defining a fiber optic light carrying bundle formed of a plurality of optical fibers each of which have a distal end. The fiber optic bundle has a proximal end which is adapted to be operatively coupled to a light source and a distal end which is located in the distal section of the sheath tube contiguous the distal lens. The fiber optic bundle has a selected number of the distal ends of the plurality of optical fibers treated to form an energy diverting member for directing thermal or infrared energy from light energy produced by a light source into the periphery of the distal lens to increase the temperature thereof to resist fogging of the distal lens when the distal tip of the endoscope is inserted into or located within a body cavity.

None of the known state-of-the-art laparoscopes which include a rigid elongated sheath tube includes use of the fiber optic light carrying bundle alone for defogging the distal tip of the laparoscope which occurs during a procedure due to a temperature differential between the distal tip of the laparoscope when inserted into a warm, moist cavity such as the abdomen or peritoneal cavity and the temperature of the cavity.

In the suction-irrigation handle for endoscopic surgery, the irrigation and suction channel did not include a nozzle for deflecting a fluid flow under pressure across the distal tip of the telescope to remove vision impeding material from or to prevent defogging of the distal tip of the telescope during a procedure.

The endoscope or instrument of the present invention overcomes several of the problems associated with the prior art the fogging problem. The teachings herein can be used for endoscopes generally which may be used for medical or other applications as discussed hereinbefore. The preferred embodiment of an endoscope is a laparoscope used for medical surgery. Therefore, the description hereafter is directed to a laparoscope. However, the teaching and the invention extends to any type of endoscope.

One advantage of the present invention is that the laparoscope can be inserted through a primary cannula and trocar assembly into the peritoneal cavity without the laparoscope immediately fogging at the distal end thereof after insertion and/or thereafter during the procedure.

Another advantage of the present invention is that the laparoscope has an irrigation means for applying a fluid flow under pressure across the distal lens through a nozzle to clean the lens impeding material therefrom without significantly affecting the raised temperature of the distal lens.

Another advantage of the present invention is that particulate matter, which may be tissue, protein, blood or the like resulting from the surgical procedure which adheres to or collects upon the distal end of the laparoscope impeding a passage of the optical image through the transparent member can be easily removed during the surgical procedure without interfering with the procedure. This matter can be removed by directing a fluid flow under pressure and through a nozzle across the exterior surface of the transparent member to remove the material from the distal tip and transparent member to permit the surgeon to continue viewing the operative site without the necessity of withdrawing the laparoscope from the cavity during a procedure.

Another advantage of the present invention is that the laparoscope can include an additional one or more working channels and/or an accessory channel which can be utilized for performing additional surgical procedures within the cavity under the direct vision and control of the laparoscope.

Another advantage of the present invention is that the irrigation channel can be utilized for aiming or directing along a predetermined path a fluid flow under pressure, across the tissue or organ subject to the procedure to remove organic material matter therefrom to permit the surgeon to have a clear view during the laparoscopic procedure.

Another advantage of the present invention is that the irrigation channel can be utilized with a high pressure fluid source to perform hydro-dissection of tissue under direct visualization of the laparoscope.

Another advantage of the present invention is that the laparoscope can include one or more working channels of various sizes. The working channels can be of the same size or can be of different sizes. The accessory channels or working channel of the laparoscope can be utilized for performing a plurality of procedures including passage of working tools such as an elongated tube or a laser guide through the channel to the operative site, thereby enabling a surgeon to utilize a laser as part of the operative surgery.

Another advantage of the present invention is that the working channel or accessory channel can be utilized with other probes, such as, for example, a coagulation probe or a BICAP® electrosurgical probe.

Another advantage of the present invention is that the channel utilized for directing a fluid flow across the exterior surface of the transparent member can be utilized for any type of fluid such as a saline solution or an appropriate gas. The laparoscope can be structured to have two separate channels, each of which has a nozzle for directing two different type of fluid flows across the exterior surface of the transparent member, such as, for example, a saline solution through one fluid flow channel and a gas fluid through the other channel.

Another advantage of the present invention is that the step of irrigating a working site or the performing of certain procedures which require "triangulation" can be eliminated. Triangulation is required when one or more instruments are inserted into a cavity through different openings and the distal ends of each instrument are direct at appropriate angles to the operative site. Triangulation is usually required to irrigate an operative site by inserting an irrigation tool through one opening and inserting a laparoscope through a second opening. By using the teachings of the present invention in a laparoscope having an irrigation channel or working channels, all channels are in substantial parallel alignment with the elongated axis of the rigid elongated sheath and certain procedures without the triangulation step.

Another advantage of the present invention is a method for performing laparoscopic surgery utilizing the laparoscope of the present invention which includes inserting the laparoscope into the peritoneal cavity wherein the distal lens resists fogging, applying a fluid flow across the distal tip of the laparoscope to remove image impeding agents therefrom and for viewing the surgical site through the laparoscope as shown.

Another advantage of the present invention is that a method for performing surgery utilizing the laparoscope of the present invention having a distally heated distal lens can include utilizing a laparoscope having an accessory channel or working channel which is capable of passing accessories therethrough for performing surgical procedures under direct visualization of the laparoscope. During the procedure, as impeding agents, such as protein material, tissue material or the like is deposited upon the distal lens, by use of the distal nozzle for directing a fluid flow across the exterior surface of the transparent member, the surgeon can perform the entire laparoscopic procedure without removing the instrument therefrom until the completion of the surgery.

Another advantage of the present invention is that the method for performing laparoscopic surgery utilizing a laparoscope having a distally heated distal lens and the distal nozzle fluid flow washing means of the present invention, can perform the surgical procedure more efficiently without the requirement that the laparoscope be removed from the peritoneal cavity during the procedure thereby decreasing the time required for a surgeon to complete a procedure.

Another advantage of the present invention is that when a saline solution is used by the lens washing system, a short burst of fluid is used as the lens rinse actuation to impinge fluid upon and clean the material off of the lens. Usually, very small droplets of fluid remain on the surface of the distal lens. The infrared radiation from the light energy, diverted by the treated distal ends of the optical fibers, dry the very small droplets causing the same to disappear very quickly. However, if the volume or size of the droplets are larger, it may be necessary to use a lens wash to provide complete removal of the droplets.

Another advantage of the present invention is that acceptable heating and temperature levels for the distal lens can be obtained with deformation or blocking of approximately 20% of the optical fibers of a fiber optic light carrying bundle. The remaining unblocked optical fibers are adequate to illuminate the operative side for imaging including video imaging.

Another advantage of the present invention is that the laparoscope using the distally heated lens of the present invention and having a distal nozzle and working and/or accessories channels can form part of a system for performing laparoscopic procedures.

BRIEF DESCRIPTION OF THE DRAWINGS

These and other advantages of the invention will be readily apparent when considered in light of the detailed description hereinafter of the preferred embodiment and of the drawings which include the following figures:

FIG. 1 is a bottom, front and left end perspective view of a laparoscope having a distal heated distal lens washing means and a working channel;

FIG. 2 is a partial top plan sectional view showing the proximal end of a laparoscope for practicing this invention;

FIG. 3 is a distal section perspective view of one embodiment of the laparoscope of FIG. 1 showing a distal tip having a distal end heating means in the form of annular segments, a transparent member for passing an optical image and a nozzle for directing different a fluid flow across the exterior surface of the transparent member;

FIG. 4 is a distal end elevational view showing a laparoscope having the distal end heater and a single nozzle for directing a fluid flow across the exterior surface of a distal lens;

FIG. 5 is a partial from view of a sub-assembly formed of an image transferring means channel and having a fluid flow channel which is operatively connected to and which extends from the proximal end to the distal end of the laparoscope;

FIG. 6 is a partial proximal end elevational view showing the extended housing and one trumpet valve operatively connected to the means for defining an opening which is operatively connected to the fluid flow channel to conduct pressurized fluid flow to the nozzle located at the distal end of the laparoscope;

FIG. 7 is a partial cross-sectional side elevational view showing an endoscope extended housing section of the extension member which operatively attached to the proximal end of the rigid elongated sheath tube and showing the relationship between a light post adapted to be connected to a light source and a means for defining an opening which is operatively connected to a fluid flow channel and valve means which terminates in a nozzle at the distal end of the laparoscope and the generic structure of the distal end having the distal end heating means;

FIG. 8 is a partial cross-sectional view of the structure of the distal end of the endoscope housing of the embodiment illustrated in FIG. 7;

FIG. 9 is a pictorial representation of the distal end of the laparoscope showing the relationship between the treated distal ends of the fiber optic bundle, the nozzle and the distal lens;

FIG. 10 is a partial cross-sectional view of the fiber optic light carrying bundle at the distal end taken along section of lines 10—10 of FIG. 9;

FIG. 11 is a partial side cross-sectional view showing the preferred embodiment of a structure of the nozzle taken along section line 11—11 of FIG. 9 for producing a shaped fluid discharge from the nozzle;

FIG. 12 is a pictorial representation partially in cross-section of the distal tip of an endoscope showing the preferred embodiment of a conductive member positioned adjacent the treated distal ends of the optical fibers to conduct thermal or infrared energy from treated distal ends of optical fibers to a distal lens;

FIGS. 13(a), 13(b) and 13(c) are pictorial representations of various means of treating distal ends of optical fibers and for forming a thermally conductive means therebetween;

FIG. 14 is a partial left side front elevational view of a distal end of a laparoscope having treated distal ends of a fiber optic light carrying bundle having a thermally conductive member and wherein the distal lens is at an angle;

FIG. 15 is a pictorial representation of an individual optical fiber formed of a core glass and cladding glass to control emissions of light from the end of the optical fiber;

FIG. 16 is a pictorial representation of an optical fiber wherein a portion of the cladding glass is removed as one embodiment of treatment of the distal end of the optical fiber;

FIGS. 17(a), 17(b) and 17(c) are pictorial representations of the several methods for treating an optical fiber to remove the cladding glass and expose the core glass to produce a treated distal end;

FIG. 18 is a graph of temperature (° C.) verses time in minutes required for heating the distal tip of a laparoscope using the structure of FIG. 12;

FIGS. 19(a), 19(b) and 19(c) illustrate steps of an alternate method of treating a selected number of optical fibers of the fiber optic light carrying bundle showing the beginning shaping of the bundle, the formulation of a partial annular slot in the distal end of the bundle and the filling of the partial annual slot with a conducting epoxy;

FIG. 20 is a pictorial representation of a distal end of a laparoscope having a pair of opposed partial annular slots formed using the method steps illustrated in FIGS., 19(a), 19(b) and 19(c).

FIG. 21 is a right end plan view of one embodiment of a laparoscope having a distal end heating means formed by a conductive member in the form of a pair of annular shaped segments;

FIG. 22 is a partial cross-sectional view taken along section lines 22—22 of FIG. 21;

FIG. 23 is a partial cross-sectional view taken along section lines 23—23 of FIG. 21;

FIG. 24 is a top right end plan view of another embodiment of a laparoscope having a distal end heating means formed by a conductive member in the form of a pair of annular shaped segments and a distal lens washing nozzle;

FIG. 25 is a partial cross-sectional view taken along section lines 25—25 of FIG. 25;

FIG. 26 is a partial cross-sectional view taken along section lines 26—26 of FIG. 26;

FIG. 27 is a top view of a lens tube;

FIG. 28 is a right side elevational view of the lens tube in FIG. 27;

FIG. 29 is a front elevational view of the lens tube of FIG. 28; and

FIG. 30 is a partial cross-sectional view of a subassembly formed of an extended tube enclosing a fiber optic light carrying bundle and a lens tube.

DESCRIPTION OF THE PREFERRED EMBODIMENT

Typically, endoscopes are assembled or fabricated with a fiber optic light guide bundle having a proximal end and a distal end. This proximal end of the fiber optic light guide bundle is operatively connected to a light source. The distal end of the fiber optic light guide typically uses the visible light to illuminate an operative site.

Light sources used in surgical operating environments generate an output light having a broad band wavelength from the ultraviolet (UV) band, through the visible light band and near and short infrared band (IR). Lamps used in such light sources produce energy over wavelength less than 0.3 microns to beyond 20 microns. Fiber optic bundles can be damaged in the temperatures thereof approach or exceed 275° F. (135° C.). Some light sources include infrared filters to filter out or remove sufficient IR to prevent the temperature from approaching or exceeding 275° F. (135° C.).

In the present invention, the temperature of the distal end required to resist fogging of the distal lens is approximately 88° F. (31° C.). The preferred temperature range for the distal lens to resist fogging is from about 88° F. (31° C.) to about 107° F. (42° C.). This provides a safety bandwidth of about 19° F. (11° C.).

Optical fiber temperatures at the light guide/light post interface required to heat the distal lens to the required temperature range to resist fogging will be from approximately 175° F. (80° C.) to approximately 225° F. (107° C.). The bandwidth is 50° F. (28°C.) and the maximum temperature does not exceed 275° F. (135° C.) thereby preventing thermal damage to the optical fibers.

In the preferred embodiment, the laparoscope utilizing this invention is used in the pneumo peritoneum cavity which typically has a humidity of between about 90% to 100%. However, it is envisioned that an instrument using the teaching of this invention would be used in applications having substantially lower humidity.

The terms "thermal energy" or "infrared energy" as used herein is intended to describe the energy from a light source which is the source of thermal energy used to heat the distal lens as described herein.

The light source for practicing this invention may be any commercially used light source adopted for use with an endoscope such as, for example, a halogen source, a xenon light source, a CIRCON ACMI MV9082 metal halide light source or a light source having mercury lamps.

FIG. 1 illustrates an endoscope or instrument, shown generally as 30 which, in the preferred embodiment is a laparoscope, for practicing the present invention. The instrument 30 includes a rigid elongated sheath tube 32 having a selected length and a distal section or end 36 and a proximal section or end 38. The distal end 36 terminates in a distal tip shown generally as 44. The interior of the laparoscope includes image transferring means for transferring an image from the distal tip 44 through the rigid elongated sheath tube 32 to the proximal end 38 of the laparoscope. The image transferring means is typically surrounded by fiber optic light carrying means generally referred to as fiber optic light guides or fiber optic light carrying bundle. This is illustrated in greater detail in FIGS. 3 and 4.

The proximal end 38 of the laparoscope is operatively connected to an extension member shown generally as 48. The extension member 48 includes means for supporting a light post 52 and means for defining openings or ports for two channels, which openings are shown as 54 and 60 (60 being visible in FIG. 2). Valve means, which in the preferred embodiment are trumpet valves 58 and 62, are operatively connected to openings 54 and 60, respectively. An eyepiece housing, shown generally as 64, terminates in an eyepiece 66 which permits a surgeon to view the optical image transferred through the laparoscope. Also, it is well known in the art that a video camera 68, which is shown by dashed lines, can be operatively connected to the eyepiece 66 to convert the optical image into a video signal which is ultimately processed by a video processing means to produce a video image on a monitor or video signals for storage of the video image on magnetic tape or other storage means.

The laparoscope 30 may include a plurality of channels which can be used for a number of functions. Several species of laparoscopes are disclosed herein. It is envisioned that a laparoscope of the present invention could include a working or accessory channel having a dimension sufficient to pass an elongated tube which could extend up to the distal end 44. The elongated tube could be used for a number of functions, such as for suction. For example, the elongated tube could extend parallel to the center axis of the imaging means, depicted by dashed line 34, which is co-axial with the elongated axis of the elongated sheath tube. The end of the elongated tube could be used to direct fluid onto the operative site while keeping the distal end 44 away from possible splashing of the fluid and concurrently enabling the user to view the operating site. As illustrated in FIG. 1, the central axis of the imaging means is co-axially aligned with the elongated axis of the elongated sheath tube 32 and shown with an offset of zero. However, the central axis 34 could have a preselected offset relative to the elongated axis of the elongated sheath tube 32. This would permit larger working channels. The size of the working channels may be the same, or one channel could be smaller than the other. Sizes in the order of 1 mm and 2 mm are typical. The overall length of the laparoscope could be between about 150 mm to about 350 mm with about 300 mm being preferred.

Also, in certain instances, the elongated tube depicted could be used to pass working accessories such as, for example, a laser guide depicted by dashed line 46 shown in FIG. 2. The elongated tube could be extended manually or the laparoscope could include a means for extending the elongated tube.

The preferred embodiment for practicing this invention is as a rigid endoscope. However, the teaching of this invention could be used in any known endoscope having an outer wall, fiber optic light guide, image transferring member which terminates in a transparent member located at the distal end thereof. Such endoscope would include rigid, semi rigid or flexible endoscopes.

FIG. 2 shows in greater detail the structure of the extension member 48 and the relationship between the means for defining openings 54 and 60, the trumpet valves 58 and 62 and the relationship therebetween to the eyepiece housing 64. Also, an eye is depicted as 67 to enable a user to view an image through the eyepiece 66.

FIG. 3 shows one embodiment of a distal end of a laparoscope utilizing the teachings of the present invention. In the embodiment of FIG. 3, the distal tip 44 includes means, which are located within an outer tube, which define the rigid elongated sheath tube 32. The sheath tube 32 includes a distal end 36 and a nozzle 82 which provides a means for directing a fluid flow across the exterior surface of a transparent member or an image passing means shown generally as 80. In the embodiment, the transparent member is a distal lens. Image passing means 80 is located in the center of a lens tube 74.

As illustrated in FIG. 3, the distal section 44 of the sheath tube 32 includes means for defining a fiber optic light carrying bundle formed of a plurality of optical fibers each of which have a distal end. The fiber optic light carrying bundle has a proximal end which terminates in light post 52 (shown in FIG. 1) which is adapted to be operatively coupled to a light source shown by arrow 126 in FIG. 7. The light energy from the light source 126 has thermal or infrared energy which can be diverted and used to heat the distal end of the laparoscope. The fiber optic light carrying bundle has a distal end shown generally as 70 which is located in the distal section 44 of the sheath tube 32. The fiber optic bundle has a selected member of the distal ends of the plurality of optical fibers heated to form a light diverting member for directing thermal energy from a light source 126 into a periphery of the image transferring means 80. The annular shaped conducting segments shown by 76 and 78 couple the treated distal ends to the distal lens represented by image transferring means 80. Thus, the portion of the fiber optic light bundle shown by 70 located between segments 76 and 78 and the distal section 44 provide the illumination for the operative site. An irrigation channel 84 is shown opposite the nozzle 82. The objective cell for the lens is shown by 92.

FIG. 3 illustrates the use of annular segments 76 and 78 which are formed of a thermally conductive material which are used to couple thermal energy from the treated ends of a fiber optic bundle 70 to the image transferring means 80. Although FIG. 3 shows one embodiment of a laparoscope having annular segments 76 and 78, other embodiments may be used. For example, FIG. 12 uses a thermally conductive material in the form of a ring.

In practicing this invention, the thermally conductive material must function as a sealant, adhesive or binding agent, have a minimal thermal conductive to effectively couple the thermal energy from the treated ends of the fiber optic bundle to the distal lens or other transparent member and must biologically compatible with the human body. The thermal conductivity of the thermally conductive material, at a minimum, should be about 10 BTU/hour/ft$^2$/inch/° F. However, it is preferable that the thermal conductive level be higher, such as, for example, in the order of about 25 to about 27 BTU/hour/ft$^2$/inch/° F. The use of a conductive epoxy is one material that can be used satisfactorily, but any material having the desired properties or characteristics may be used as well. For example, a metal material, ceramic material or other adhesive having the above properties could be used.

The desired temperature to which the distal end is heated is the temperature at which the distal lens resists fogging when the distal end of the laparoscope is inserted into a body cavity. The preferred temperature range is from about 31° C. to about 37° C.

The above is accomplished by deforming, blocking or otherwise treating a selected percentage or number of the distal ends of the plurality of optical fibers to form a light diverting member for directing thermal or infrared energy from a light source into the distal lens or other member which cooperates with the image transferring means 80.

The heated conductive segments 76 and 78 are located between the coaxially aligned lens tube 74 and the image transferring means 80. The remaining untreated distal ends 70 of the fiber optic bundles are located between the lens tube 74 and the outer tube or distal section 44 of the sheath tube 32 and surround both the nozzle 80 and the irrigation tube 84. The remaining untreated distal ends 70 of the fiber optic bundles fill the annular space between the head conductive segment 76 and 78. The laparoscope of the embodiment of FIG. 3 is a 10 mm diameter scope with a 0° lens and has lens washing capability. However, it is within the teachings of this invention that the distal tip heating means could be used in laparoscopes without the lens washing capability.

In FIG. 3, the image passing means may be a distal lens, a window for a charge coupled device, window for a video sensor or the like. A laparoscope having a video sensor located at its distal end may be known as a video laparoscope.

Also, in FIG. 3, the means for directing a fluid flow across the exterior surface is shown generally as nozzle 82. Nozzle 82 is operatively connected to a means for forming a fluid flow channel which extends from the distal tip 44 of the laparoscope to the proximal end of the elongated sheath tube 32. The nozzle 80 is designed to direct the fluid flow in a wedge-shaped flow pattern and at an angle substantially normal to the axis of the rigid elongated sheath tube 32. The nozzle 82 is located in the outer space between lens tube 74 and distal section 44 which encloses the untreated distal ends 70 of the distal end 70 of the fiber optic light guide means.

In the embodiment of FIG. 3, a second channel shown as circle 84 may be used as a working channel for passing instruments or as a fluid flow channel, and if a fluid flow channel, then the same would terminate in a second nozzle. In the embodiment of FIG. 3, the channel and/or nozzle shown by 84 can be utilized for one type of fluid flow, such as, for example, a saline solution under a pressure of approximately 300 millimeters of Hg.

The pressure range could be in the order of about 200 millimeters of Hg to about 350 millimeters of Hg with about 300 millimeters of Hg being preferred. The lower the pressure, the less cleansing action occurs. The fluid could be any appropriate solution other than a saline solution. Pressures greater than 350 millimeters of Hg. could be used depending on the procedure.

Also, the channel and/or nozzle shown by 84 can be operatively connected to an alternate source of fluid, such as, for example, a carbon dioxide ($CO_2$) gas. The surgeon, by use of the appropriate valve means, can selectively direct a flow of saline or a flow of gas through the second channel and/or nozzle shown by 84 or direct saline and/or gas across the exterior surface of the image passing means 80 through nozzle 82 to remove image impeding agents therefrom. In the embodiment of FIG. 3, the image passing means is in the form of a transparent member 80 which is adapted to pass an optical image therethrough to an image transferring means which transfers the image to the proximal end 38 of the laparoscope where the image is received by an eyepiece 66. At the eyepiece 66, the image is directly viewable by a surgeon, or the image can be utilized as an optical image input to a video camera, shown as 68 in FIG. 1.

FIG. 4 illustrates and end view of the preferred embodiment of a laparoscope having the distally heated distal end and having a nozzle 82 as a lens washing means depicted in FIG. 3. The lens tube 74 is partially exposed as shown in FIG. 4. The conductive segments 76 and 78 located in the space between the lens tube 74 and transparent member 80 are coupled to the treated distal ends located thereunder of the fiber optic light carrying bundle. The untreated distal ends of the remaining of the plurality of optical fibers shown as 70 and are located between the outer tube or sheath tube 44 and the lens tube 74. In the preferred embodiment, approximately 20% of the optical fibers distal ends are treated. As such, the remaining approximately 80% of the optical fibers depicted by element 70 form a light guide to illuminate the operative site.

FIG. 5 depicts in greater detail, the structure of extension member 48 in its relationship to the rigid elongated sheath tube 32. Specifically, the proximal end 38 of the rigid elongated sheath tube 32 is operatively connected to the extension member 48. A light post 52 is positioned to be operatively attached to the extension member 48. The fiber optic light guide means is located in light post 52 and is interspersed within the laparoscope as described in connection with FIGS. 1 through 4. In the embodiment illustrated in FIG. 5, the light post 52 is depicted to extend normally from the extension member 48. However, it is envisioned that the light post 52 could take other physical shapes, such as, for example, the light post 52 could be in the form of an elbow having a 90° deflection and which extends in a direction towards the upper housing section 124.

Also, the means for defining opening or ports 54 and 60 for the fluid flow channel and the irrigation channel, respectively, are operatively connected to the extension member 48. The upper portion 124 of the extension member 48 is adapted to be operatively connected to an eyepiece 66 as depicted in FIG. 1 or to any other type of optical image receiving means such as, for example, a video camera.

FIG. 6 shows a partial proximal end elevational view of the assembly illustrated in FIG. 5 and shows in greater detail that the light post 52 extends in a substantially normal direction from the extension member 48. The upper portion 124 of the extension member 48 is adapted to be operatively connected to an eyepiece as described hereinbefore. The means for defining an output or port 60 and the means for defining an output or port 54 are adapted to be operatively connected to a valving means. In FIGS. 5 and 6, the preferred means for defining valving means is a trumpet valve 58. However, it is envisioned that any type of valving means could be used such as, for example, a stop cock valve.

FIG. 7 illustrates in greater detail the structure of the rigid elongated sheath tube 32 and the location or position of the various elements within the sheath tube. As depicted in FIG. 6, the distal section 36 includes a fluid flow channel 140 which terminates in the nozzle 82. The fluid flow channel 140 includes a proximal section 146 which extends through the extension member 48 and into an operative connection with the means for defining an outlet or port 54. Port 54 is operatively connected to the extension member 48 through any known connecting means such as, for example, a threaded connecting means. In the preferred embodiment, a trumpet valve fluid control means 58 is fastened to port 54.

The light post 52 supports the fiber optic light guide elements 120 which is then interspersed within the space existing between the exterior surface of the image transferring means channel 142 and the inner surface of the rigid elongated sheath tube 32. The light post 52 is adapted to be operatively connected to a light source depicted by arrow 126. One example of a light source that may be used is a Circon Model MV-9082 fiber optic light source and Circon Model G-96 6 mm light guide.

The proximal end 148 of the image transferring means channel 142 communicates with the portion of the extension member 48 as depicted in FIG. 6.

FIG. 8 illustrates the detail of how the fibers of the fiber optic light carrying bundle 70 are distributed and the lens tube 74, the nozzle 80 and its associated channel and the irrigation channel 84. The image transferring means 130 is located within the lens tube 74. The image transferring means 130 may be any known lens system utilized in an endoscope and could include, without limitation, rod relay lens system, solid lens system, grin lens system and the like.

Referring to FIG. 9, the distal section 44 is spaced a predetermined distance from the lens tube 74 (shown as a dashed circle) to define an outer annular shaped slot which is adapted to receive and have inter-dispersed therein the distal end of the untreated optical fiber. In the preferred embodiment, approximately 80% of the optical fibers forming the fiber optic light carrying handle are positioned in the outer annular shaped slot.

The lens tube 74 is located below the conductive epoxy layer 76 and the outer edge of the lens tube 74, is essentially co-planar with the treated distal ends of the fiber optic light carrying bundle. The treated distal end of the selected number of the plurality of the optical fibers are located herein. The treated distal ends are deformed, blocked or otherwise treated to define a light diverting member so that a sufficient portion of the light energy and thermal energy of the light source is available to distally heat the transparent member or distal lens to a sufficiently high temperature, say in the order to about 31° C. to about 37° C. for a period of about 4 minutes or more before use of the laparoscope in a laparoscopic procedure.

The treated distal ends of the selected number of the plurality of fibers can be treated in a different number of ways to form the light diverging distal ends.

For example, FIG. 10 is a partial cross-sectional view showing the relationship and structure of the untreated or remaining distal ends 70 of the fiber optic light carrying bundle and the treated distal ends 76 of the selected number of the plurality of optical fibers. In FIG. 10, each of the treated distal ends 76 of the selected number of optical fibers is disposed away from the distal ends 70 of the remaining fiber optic bundle. The cladding glass still encloses the core glass up to the distal end of the core glass.

In FIG. 10, a layer of a special conductive epoxy 180, such as for example, Master Bond Supreme 11 ANHT is applied to the distal ends 76 to thermally couple the end thereof, the conductive epoxy 180 covers the end of the lens tube 74 and encloses the transparent member 80. The width of the layer of spaced epoxy may be in the order of about 0.010 inches.

FIG. 11 shows in greater detail, the relationship between the distal end of the laparoscope 44, the fluid flow channel 140 and the nozzle 82. The nozzle 82 has its deflecting head 170 extending or protruding slightly therefrom and positioning the dispensing slot 172 so as to be able to direct the spray across the transparent member 80 as depicted in FIG. 9. The nozzle 82 includes a channel 176 which conducts fluid flow from the fluid flow channel 140 through the head 170 and into communication with the dispensing slot 172.

FIG. 12 shown another embodiment of the present invention wherein the treated distal end of the selected member of the plurality of optical fibers, formed of a cladding glass enclosing the core glass, has a preselected portion of the cladding glass removed therefrom. The treated distal ends 76 are embedded with a conductive epoxy 180, such as, for example, Master Bond Supreme 11 ANHT.

The conductive epoxy material 180 or substantially equivalent material, functions as a thermally conductive medium to conduct or carry infrared energy to and increase the temperature of the transparent member 80 which in this embodiment is a distal lens.

Therefore, it is desirable to have the conductive epoxy 180 in communication with the distal ends 76 to conduct thermal energy therefrom to the transparent member 80, which preferably is a distal lens.

FIGS. 13(a) shows pictorially that the distal end of a selected optical fiber 188 which has the cladding glass 190 removed from the end thereof exposing core glass 192.

In this embodiment, the core glass protrusion has a selected length so as to extend part way into the conductive epoxy material 180.

FIG. 13(b) shows an alternate embodiment wherein the length of the selected distal ends of the selected optical fibers 188 are cut short and the conductive epoxy 180 is located thereon. If desired, a special epoxy similar to the coupling epoxy 180 of FIG. 10 could be used to increase the thermal coupling coefficient.

FIG. 13(c) show yet another embodiment where the optical fiber 188 has the cladding 190 stripped back or removed such that the length of the protrusion of core glass 192 is longer by AX which is shown as 202, than the thickness of the conductive epoxy layer 180.

FIG. 14 shows yet another embodiment where the distal section 210 of a laparoscope has an angle formed thereon as depicted by angle α shown by dashed lines 236 and 238. In the preferred embodiment, α is 30°. However, the angle α can be from 0° to about 30°. As such, the length of the untreated distal ends 212 of the fiber optic light carrying bundle would be different, but are still located in the outer annular slot defined between distal section 210 and the lens tube 214. The length of each of the treated distal ends 232 are substantially the same. The spacing or distance from the distal ends 232 to the inclined edge of the distal edge and around the distal lens 230 is filled with a conductive epoxy 216. As shown in FIG. 14, the thickness of the epoxy 216 adjacent the angle α is controlled and an insulator material 218 is used to capture the thermal energy within the epoxy material 216 to heat the lens 230.

FIG. 15 illustrates pictorially how an optical fiber shown generally as 188 emits light energy. The core glass 222 has an index of refraction of $N_1$ and the cladding glass has an index of refraction of $N_2$. The light energy traverses a path shown as line 224. When the light energy including the infrared energy reaches the outer surfaces of the core glass 220, the energy is reflected internally back into the core glass 222 until the light energy reaches the end of the core glass where it exits out of end thereof as shown by arrow 226 and into air having an index of refraction of $N_3$. If a conductive epoxy or other thermally conductive member is positioned at the end of the core glass 222, the light and thermal energy depicted by arrow 226 would be coupled into the thermally conductive material, such as depicted by FIGS. 13(b) and 13(c).

FIG. 16 illustrates pictorially how an optical fiber shown generally as 188 emits light energy when the cladding glass 220 is removed resulting in the distal end of the core glass 222 extending a predetermined distance beyond the cladding glass 220 this results in the outer surface 230 being exposed to an air environment having an index of refraction of $N_3$. In this embodiment, the light energy 224 is reflected internally by the cladding glass 220 until the cladding glass is replaced by air resulting in the light and thermal energy exiting radially from the outer surface 230 of the core glass 222. This may be referred to as light energy being emitted radially from the optical fiber. Since the index of refraction of air is $N_3$, the path traversed by the light and thermal energy is depicted by arrow 232.

FIGS. 17(a), 17(b) and 17(c) pictorially represent several methods for removing the cladding glass 222 of the optical fiber 188 from the core glass 222.

FIG. 17(a) depicts the step of preparing the optical glass fiber 188 where the distal end thereof has a relatively planar surface such that the end of the core glass 222 and the edge of the cladding 220 are substantially planar.

FIG. 17(b) depicts the step of removing from a selected number of distal ends of the plurality of optical fibers a predetermined length or section of the cladding glass 240 from the core glass to enable thermal energy to exit the core glass radially through an outer surface of the core glass 222.

This step of removing cladding glass can be performed by a mechanism depicted by box 242 which removes the cladding glass mechanically, including by mechanically stripping or by mechanically grinding.

Techniques for scratching and/or breaking the cladding glass using appropriate scribing tools and the like is well known to persons skilled in the art.

Alternatively, the cladding glass can be formed of an etchable cladding glass such that the same can be removed chemically, such as by chemical etching as depicted by box 244. The desired result is to have the cladding glass 230 removed a predetermined distance from the distal end of the core glass as shown in FIG. 17(c) such that an outer surface 230 of the core glass 222 is exposed to enable the exiting of light energy and thermal energy therefrom as discussed above in connection with FIG. 16.

FIG. 18 is a graph which depicts the relationship between temperature in ° C. of the distal lens verses time for heating of a distally heated laparoscope distal end using the embodiment of FIG. 12. The graph is based on about 20% of the optical fiber distal ends being deformed or obscured. The temperature measurements were made in rooms at an ambient room temperature. The rate of time required to reach the desired temperature and the level of the final temperature is determined by the intensity of the light source. A light source at an intensity I=X, as depicted by curve 260, raises the temperature to about 32° C. which is within the desired temperature range of about 30° C. to about 37° C. which is required to resists fogging when the distal end of a laparoscope inserted into a body cavity.

A light source at an intensity of I=0.8 X, as depicted by curve 262, is sufficient to raise the temperature to a level of about 30° C. which is in the lower temperature range.

Similarly, a light source at an intensity of I=1.3 X, as depicted by curve 264, clearly is sufficient to raise the temperature thereof to about 37° C. which is in the upper range of the temperature range. The upper limit of the temperature range must be selected to be a temperature which does not burn or otherwise injure the patient and/or the patient's internal organs or tissue.

FIGS. 19(a), 19(b) and 19(c) depict an alternate method for treating the distal ends 270 of a selected number of the plurality of optical fibers. This method may be performed using a milling tool for guiding a pocket in the illuminated or optical fibers.

The method comprises the steps of preparing a relative planar surface 272 on the distal end of the fiber optic light carrying bundle as shown by FIG. 19(a).

The step of forming at least a pair of spaced partial annular slots 276 in the distal end 270 of a selected number of distal ends of the plurality of optical fibers is performed as shown by FIG. 19(b) and FIG. 20. Of course, the entire annular ring could be formed, if desired. One procedure which may be used to accomplish the above is to advance a grinding tool from zone distal to the distal face of the endoscope ("head on") towards the proximal end of the endoscope and mill away a selected portion of the illuminated fibers closest to the distal lens.

The next step of filling the pair of partial annular slots 276 with a thermally conductive epoxy 278 is shown in FIG. 19(c) and FIG. 20. The conducting material is adapted to direct thermal or infrared energy from a light source into the periphery of the distal lens 280. FIG. 20 illustrates one embodiment of an endoscope so fabricated using this method.

As illustrated in FIG. 20, this embodiment depicts that the annular slots 276 are partial slots because not all of the distal ends of the fiber optic light carrying bundle in the annular ring surrounding the distal lens 280 are treated. By first forming the pair of opposed partial annular slots 276 and filling the same with conductive epoxy as shown in FIG. 19(c), a sufficient number of the distal ends of the selected number of the plurality of fiber optics are deformed or treated to divert light energy and thermal or infrared energy into the distal lens 280 to raise the temperature of the distal lens to a temperature that resists fogging when the distal end of the laparoscope is inserted into a body cavity. This structure may be used where it is desired to have more of the untreated distal ends of the fiber optic light carrying bundle illuminate the operative site.

FIGS. 21, 22 and 23 illustrate the structure of a distal tip for an endoscope having two working channels 304 and 306. The working channels 304 and 306, in this embodiment, are located in an opposed spaced relationship to each other.

In FIG. 21, the elongated tube 302 encloses a first channel member 304, a second channel member 306 and the fiber optic light carrying bundle 310. The fiber optic light carrying bundle 310 is positioned between the lens tube 316 and the elongated tube 302.

In the structure of FIG. 21, the lens tube 316 and objective cell 318 are positioned adjacent each of the channel member defining the working channels 304 and 306. Thus, the fiber optic light carrying bundle 310 is formed or distributed around the channel members 304 and 306 and in the space defined between the lens tube 316 and the extended tube 300.

The distal ends of the fiber optic light carrying bundle 310 and the outer end of the lens tube 316 and the objective cell 318 are treated to form a pair of spaced annular grooves. The depth of the grooves 320 and location of the machined end of the lens tube 316 and the objective cell 318 are shown in FIG. 23.

The grooves 320 is then filled with a conductive epoxy layer 322. The conductive epoxy layer 322 is in contact with the treated ends of the fibers 324 shown in FIG. 23, the end of the lens tube 316, the end of the objective cell 318, and the transparent member 326. As shown in FIG. 22, the transparent member 326 encloses a distal lens 328.

The conductive epoxy layer 322 conducts thermal energy from the treated distal end 324 to the transparent member 326 to increase the temperature thereof to resist fogging of the transparent member 326 that enclose the distal lens 328.

FIGS. 24, 25 and 26 illustrate the structural details of the embodiment of FIGS. 3 and 4 wherein a distal lens 86 is located rearward of the transparent member 80. The elements that are common to FIGS. 3 and 4 are identified with the same member.

The nozzle 82 and the working channel 84 are positioned adjacent the lens tube 74. Thus the end portion of the lens tube 74 located adjacent the nozzle 82 and the distal end of the working channel 84 are essentially co-planar with the transparent member 80. The fiber optic light carrying bundle 70 is formed or distributed around the nozzle 82 and the working channel 84 and in the space located between the extended tube 36 and the lens tube 74. As illustrated in FIG. 26, an annular groove 332 is formed over the area corresponding to the conductive epoxy layer 74 and 76. The result is that selected distal ends 334 of the fiber optic light carrying bundle 70 are treated in a manner similar to the structure illustrated in FIG. 13(b).

The structure of the lens tube 74 is such that the end portion thereof which define the annular grooves 334 is located under the conductive epoxy layer 76 and 78. In this manner, the conductive epoxy layers 76 and 78 conduct the thermal energy from the treated distal ends 334 to the transparent member 80 to increase the temperatures thereof to resist fogging of the transparent member 80 that includes the distal lens 86.

FIGS. 27, 28 and 29 depict the structure of an objective cell 72 used in the embodiment illustrated in FIGS. 24, 25 and 26. The objective cell 72 has a central elongated tube 340 which terminates in a distal end having a circular cross-section and a circumferential periphery having a pair of spaced, arcuate raised section 342. The raised section 342 correspond to the position of the objective cell 72 adjacent the nozzle 80 and working channel 84 as shown in FIG. 24.

The portion of the circumference of the distal edge shown as 346 is used as and defines part of the annular groove 334 as shown in FIG. 26.

FIG. 30 is a partial assembly view of the extended tube 36 having fiber optic light carrying bundle 70 and the lens tube 74 located therein. The raised section 342 of the lens tube 74 enclose the transparent member as illustrated in FIG. 24. The treated distal end 334 of the fiber optic light carrying bundle 70 are generally co-planar with the circumferential edge 346.

After the transparent member 80 is assembled into the subassembly, the annular groove 332 is ultimately filled with the conductive epoxy layer to form the annular section as illustrated in FIG. 24.

The laparoscope, method and system described herein have applications for performing a wide variety of surgical procedures. Although the preferred embodiment includes use of a laparoscope which is adapted for performing surgical procedures in the peritoneal cavity, it is readily apparent that the laparoscope and its associated components could be utilized for performing procedures within other warm, moist cavities, such as body cavities or a chest cavity. Preferably, the laparoscope is used for the specific application of performing a laparoscopic cholecystectomy, that is for removing the gallbladder. However, it is envisioned that the same system, method and apparatus could be utilized for removing other organs, such as, for example, the appendix and/or kidney, or to excise tissue, to remove portions of the liver or other organs or tissue located within the peritoneal cavity. Thus, by using the teachings of the present inventory, the surgeon can attach the laparoscope having the distally heated distal lens to a light source with the intensity at approximately 80% to approximately 130% for a period of about 4 minutes to about 10 minutes or more, the temperature of the distal lens has been raised to a temperature level where the distal lens resists fogging when the distal end of the laparoscope is passed through a cannula into a body cavity at the beginning of a surgical procedure, which is the most likely condition under which fogging occurs. Further, during this procedure, the temperature of the distal lens remains at the raised temperature level thereby resisting fogging occurring or reoccurring during the entire surgical procedure. When the lens washing means system is enabled or used, a short burst of saline solution is directed across the lens to remove the impeding material. The duration of the short burst of saline does not significantly lower the temperature of the distal lens so that the temperature of the distal lens remains at the raised temperature level during the entire procedure.

The source of fluid can be a wide variety of sources and can be other than a saline solution. The pressure flow rates and pressures desired for hydro-dissection is a function of the design characteristics of the system.

Also, the working and/or irrigation channels could be utilized for other functions, such as for passing small working tools, suction, or other procedures. Also, the laparoscope can be fabricated such that the center line of the image transferring means channel, can be offset to the elongated axis of the rigid elongated sheath tube to provide the enlarged space to receive a larger accessory or working channel as described herein and as depicted in FIG. 1 hereof.

A trade off exists since a reduced number of fiber optic elements of the fiber light guide means would exist on one side of the distal end, which could degrade the optical image on one side. Also, more than three channels could be provided in the space provided between the exterior surface of the image transferring means channel and the inside interior surface of the rigid elongated sheath tube. The channels could be positioned at any angle relative each other and the embodiments depicted herein are only typical of the various structure arrangements that could be utilized in a laparoscope for practicing this invention.

What is claimed is:

1. An instrument terminating in a distal section comprising a transparent member having a periphery located in the distal section of the instrument;

a fiber optic light carrying bundle formed of a plurality of optical fibers each of which have a distal end, said fiber optic bundle having a proximal end which is adapted to be operatively coupled to a light source producing energy at different wave lengths and a distal end which is located in the distal section of an instrument contiguous to the transparent member, said fiber optic bundle having a selected number of the distal ends of said plurality of optical fibers operatively coupled to a thermally conductive material located around a portion of the periphery of the transparent member to form an energy diverting member for directing infrared energy from a light source onto the periphery of transparent member to increase the temperature thereof.

2. The instrument of claim 1 wherein each of the optical fibers is formed of a core glass enclosed by a cladding glass and wherein each of the treated distal ends of each of the selected number of optical fibers has the cladding glass removed from the core glass enabling thermal energy to exit from an outer surface of a core glass into said thermally conductive material.

3. The instrument of claim 2 further comprising an annular segment located within said distal section and formed around and spaced from the periphery of said transparent member, said annular segment having the distal ends of the selected number of the optical fibers located therein; and said thermally conductive member operatively coupled to the distal ends of the selected optical fibers and to the periphery of said transparent member for conducting infrared energy from the distal ends of the selected optical fibers to the said transparent member.

4. The instrument of claim 1 wherein the distal ends of each of the selected number of optical fibers are spaced from the distal ends of the remaining optical fibers.

5. The instrument of claim 4 wherein said transparent member is a distal lens and wherein said thermally conductive material is operatively coupled to the distal ends of the selected optical fibers and to the periphery of the distal lens for conducting infrared energy from the distal ends of the selected optical fibers to the distal lens.

6. The instrument of claim 5 further comprising an annular slot located within said distal section formed around and spaced from the periphery of the distal lens for receiving said thermally conductive material, said annular slot having the distal ends of the selected number of the optical fibers located therein and communicating with said thermally conductive material which is operatively coupled to a portion of the periphery of the distal lens.

7. The instrument of claim 6 wherein the instrument has an outer wall and wherein the remaining distal ends of the fiber optic bundle are located between the outer wall and the annular slot.

8. The instrument of claim 1 wherein the distal ends of the fiber optic light carrying bundle define an annular segment.

9. The instrument of claim 8 wherein the annular segment is filled with a thermally conductive epoxy.

10. The instrument of claim 9 wherein the distal ends of the fiber optic bundle define a pair of opposed, partial annular slot segments positioned one on each side of the periphery of a transparent member.

11. An instrument comprising an elongated sheath tube having a selected length and a distal end, said distal end including means for passing an image, said image passing means having an exterior transparent surface located at said distal end; and means defining a fiber optic light carrying bundle formed of a plurality of optical fibers each of which have a distal end for carrying infrared energy, said fiber optic bundle having a proximal end which is adapted to be operatively coupled to a light source and a distal end which is located in the distal section of the sheath tube contiguous an exterior transparent surface, said means defining a fiber optic light carrying bundle having a selected number of the distal ends of said plurality of optical fibers operatively coupled to a thermally conductive material located around a portion of the periphery of said exterior transparent surface to form a light diverting member for directing infrared energy from a light source onto the periphery of the exterior transparent surface to increase the temperature thereof.

12. The instrument of claim 11 further comprising
means located within said elongated sheath tube for defining at said distal end a means for directing a fluid flow across said exterior transparent surface of said image passing means to remove therefrom image impeding agents.

13. A laparoscope comprising
a rigid elongated sheath tube having a selected length and a distal section, said distal section having a means for defining a distal tip including a fluid tight, distal lens capable of passing an optical image, said distal lens having an exterior surface located at said distal tip; and
means defining a fiber optic light carrying bundle formed of a plurality of optical fibers each of which have a distal end for carrying infrared energy, said fiber optic bundle having a proximal end which is adapted to be operatively coupled to a light source and a distal end which is located in the distal section of the sheath tube contiguous the exterior surface of a distal lens, said means defining a fiber optic light carrying bundle having a selected number of the distal ends of said plurality of optical fibers operatively coupled to a thermally conductive material located around a portion of the periphery of the distal lens to form a light diverting member for directing infrared energy from a light source into a distal lens to increase the temperature thereof to a temperature at which a distal lens resists fogging when a distal end of a laparoscope is inserted into a body cavity.

14. The laparoscope of claim 13 wherein said distal tip terminates in a generally rounded cross-section.

15. The laparoscope of claim 13 wherein said rigid elongated sheath tube includes proximal end and further includes
a first channel which extends axially from the proximal end of the rigid elongated sheath tube to the distal tip thereof, said first channel being operatively coupled to a nozzle.

16. The laparoscope of claim 15 wherein said first channel includes at its proximal end an opening which is adapted to be operatively connected to a source of fluid.

17. The laparoscope of claim 16 wherein said opening is operatively connected to a valve means for selectively applying fluid from the source of fluid through said first channel to said nozzle to produce a fluid flow across the exterior surface of said distal lens.

18. The laparoscope of claim 17 wherein the source of fluid is under a predetermined pressure.

19. The laparoscope of claim 17 wherein said fluid is a saline solution which is under a mm of re in the order of about 300 mm of Hg.

20. The laparoscope of claim 17 wherein said valve means is a manually controlled valve.

21. The laparoscope of claim 15 further including
a second channel which extends axially from the proximal end of the rigid elongated sheath tube to the distal tip thereof; and an orifice operatively coupled to said second channel for directing a stream of fluid along a path which is substantially in alignment with the direction of view of said distal lens.

22. The laparoscope of claim 21 wherein the size of the first channel and second channel are the same.

23. The laparoscope of claim 21 wherein the size of the second channel is greater than that of the first channel.

24. The laparoscope of claim 21 wherein the interior dimension of the first channel is approximately 1 millimeter and the interior dimension of the second channel is approximately 2 millimeters.

25. The laparoscope of claim 21 wherein the exterior dimension of the rigid elongated sheath tube is approximately 10 millimeters.

26. The laparoscope of claim 25 wherein the selected length is between about 150 millimeters to about 350 millimeters.

27. The laparoscope of claim 26 wherein the selected length is about 300 millimeters.

28. The laparoscope of claim 21 wherein said rigid elongated sheath includes
at least one working channel
having interior walls; and
means for coating the interior walls of said at least one working channel with material having a reduced coefficient of friction to facilitate passage of accessories through the at least one working channel.

29. The laparoscope of claim 21 wherein said second channel includes an opening which is adapted to be operatively coupled to a pressurized source of fluid.

30. The laparoscope of claim 29 wherein said rigid elongated sheath tube include an elongated axis and said orifice is capable of directing a pressurized stream of fluid along an axis parallel to the elongated axis of said rigid elongated sheath tube.

31. The laparoscope of claim 21 wherein said rigid elongated sheath includes
at least one working channel; and
a laser guide operatively positioned within said at least one working channel, said laser guide being movable within said at least one channel to extend beyond the distal tip of said rigid elongated sheath tube.

32. The laparoscope of claim 13 further comprising
an image transferring means channel located within said rigid elongated sheath tube for receiving an image transferring means, said image transferring means channel having its distal end positioned adjacent said distal lens.

33. The laparoscope of claim 32 wherein said rigid elongated sheath tube has an elongated axis and said image transferring means channel has a central axis.

34. The laparoscope of claim 33 wherein the elongated axis of said rigid elongated sheath tube is coaxial with the central axis of the said image transferring means channel.

35. The laparoscope of claim 33 wherein said central axis of the image transferring means channel is offset from the elongated axis of said rigid elongated sheath tube.

36. The laparoscope of claim 32 further comprising
an image transferring means for passing an optical image located within the image transferring means channel.

37. The laparoscope of claim 32 wherein the rigid elongated sheath tube has an elongated axis and the distal lens is slanted relative to the elongated axis to provide a deviated direction of view having an angle of about 0 degrees to about 30 degrees.

38. A laparoscope for performing laparoscopic surgery comprising an elongated sheath having a distal end and including a fluid tight image means for passing an image, said image means having an exterior transparent surface having a periphery located at said distal end; and means defining a fiber optic light carrying bundle formed of a plurality of optical fibers each of which have a distal end for carrying infrared energy, said means defining a fiber optic light carrying bundle having a proximal end which is adapted to be operatively coupled to a light source and a distal end which is located at said distal end of the sheath tube contiguous said an exterior transparent surface, said means defining said light carrying fiber optic bundle having a selected number of the distal ends of said plurality of optical fibers operatively coupled to a thermally conductive material located around the periphery of a portion of the exterior transparent surface to form a light diverting member for directing infrared energy from a light source to the exterior surface to increase the temperature thereof.

39. A method for performing a procedure in a cavity comprising the steps of providing a laparoscope including an elongated sheath tube and means defining a fiber optic light carrying bundle for carrying infrared energy formed of a plurality of optical fibers each of which have a distal end, said means defining a fiber optic light carrying bundle having a proximal end which is adapted to be operatively coupled to a light source and a distal end which is located in the distal section of the sheath tube contiguous a distal lens having a periphery, said fiber optic bundle having a selected number of the distal ends of said plurality of optical fibers operatively coupled to a thermally conductive material located around a portion of the periphery of the distal lens to form a light diverting member for directing infrared energy from a light source into the periphery of distal lens to increase the temperature thereof;

applying light energy from a light source to the fiber optic light carrying bundle, to the thermally conductive material and onto the periphery of the distal lens for raising the temperature of the distal lens to a level that resists fogging of the distal lens when the distal end of a laparoscope is inserted into a body cavity; and viewing from the proximal section of the elongated sheath tube a body cavity through said distal lens in the laparoscope.

40. The method of claim 39 wherein the laparoscope includes a nozzle located adjacent said distal lens and further comprising the step of applying fluid under pressure through the nozzle across an exterior surface of said distal lens to remove the image impeding agents therefrom.

41. The method of claim 40 wherein the step of applying fluid under pressure includes means for directing a fluid flow of saline under a pressure of about 200 mm of Hg to about 350 mm of Hg.

42. The method of claim 40 wherein the laparoscope further includes a second channel and a working channel and further comprises the step of passing a working tool through at least one of said second channel and working channel to perform a procedure in a body.

43. The method of claim 40 further comprising the step of using the other of said second channel and working channel to perform a separate procedure in a body.

44. The method of claim 43 further comprising the step of withdrawing the laparoscope from the body cavity.

45. A system for performing laparoscopic procedures comprising a laparoscope comprising an elongated sheath tube having an elongated axis, a distal section and a proximal section which terminates in a proximal end, said distal section having a distal tip including a tight distal lens having a periphery, said distal lens having an exterior surface located at said distal tip;

means for defining an image transferring means for passing an optical image which extends from the distal tip to the proximal end of the elongated sheath tube, said image transferring means being positioned to receive an image from said distal lens;

means defining a fiber optic light carrying bundle formed of a plurality of optical fibers each of which have a distal end for carrying infrared energy, said fiber optic light carrying bundle having a proximal end which is adapted to be operatively coupled to a light source and a distal end which is located in the distal section of the sheath tube contiguous said distal lens, said fiber optic light carrying bundle having a selected number of the distal ends of said plurality of optical fibers operatively coupled to a thermally conductive material located around a portion of the periphery of the distal lens to form a light diverting member for directing infrared energy from a light source into the periphery of the distal lens to increase the temperature thereof; and a light source operatively coupled to said proximal end of the fiber optic light carrying bundle.

46. The system of claim 45 wherein the laparoscope further includes means located within said elongated sheath tube for defining at said distal tip a nozzle for directing a fluid flow across the exterior surface of said distal lens to remove therefrom optical image impeding agent.

47. The system of claim 46 wherein the laparoscope further includes a first channel which extends axially from the proximal end of the elongated sheath tube to the distal tip thereof, said first channel being operatively coupled to said means defining said nozzle, said first channel including at the proximal end an opening which is adapted to be operatively connected to a source of pressurized fluid;

a second channel which extends axially from the proximal end of the elongated sheath tube to the distal tip thereof; and means for defining an orifice for directing a stream of fluid along a path which is substantially in alignment with the direction of view of said image transferring means.

48. The system of claim 47 further including means including a video camera and video signal processing means operatively coupled to the proximal end of the laparoscope for processing a video image of the laparoscopy procedures.

49. In combination an endoscope having a distal end;

an image forming and transferring means located within said endoscope for passing an optical image and having a distal lens having a periphery; and a fiber optic light guide which directs light energy including infrared radiation out of the distal end of the endoscope, said fiber optic light guide being formed of a plurality of optical fibers each of which have a distal end, said fiber optic light guide having a proximal end which is adapted to be operatively coupled to a light source and a distal end which is located contiguous the distal lens, said fiber optic light guide having a selected number of the distal ends of said plurality of optical fibers being operatively coupled to a thermally conductive material located around a portion of the periphery of the distal lens to form a light diverting member for directing infrared energy from a light source;

said thermally conductive material absorbing and conducting infrared radiation received by said selected number of the distal ends of said plurality of optical fibers from a light source to the distal lens to raise the temperature of the distal lens to a temperature at which the distal lens will resist fogging when the distal end of the endoscope is inserted into a body cavity.

* * * * *